United States Patent [19]

Fischell

[11] Patent Number: 5,263,959
[45] Date of Patent: Nov. 23, 1993

[54] DOTTERING AUGER CATHETER SYSTEM AND METHOD

[75] Inventor: Robert E. Fischell, Dayton, Md.
[73] Assignee: Cathco, Inc., Dayton, Md.
[21] Appl. No.: 779,637
[22] Filed: Oct. 21, 1991
[51] Int. Cl.$^5$ ............................................. A61B 17/32
[52] U.S. Cl. ..................................... 606/180; 606/167
[58] Field of Search ............... 606/180, 172, 167, 192, 606/184, 185, 186; 604/53

[56] References Cited

U.S. PATENT DOCUMENTS

| | | | |
|---|---|---|---|
| 3,833,003 | 9/1974 | Taricco | 606/192 |
| 4,692,200 | 9/1987 | Powell | 606/192 |
| 4,923,462 | 5/1990 | Stevens | 606/180 |
| 5,021,044 | 6/1991 | Sharkawy | 604/53 |
| 5,030,201 | 7/1991 | Palestrant | 604/53 |
| 5,078,681 | 1/1992 | Kawashima | 604/53 |
| 5,090,958 | 2/1992 | Sahota | 606/192 |
| 5,135,525 | 8/1992 | Biscoping et al. | 606/186 |
| 5,135,535 | 8/1992 | Kramer | 606/192 |

FOREIGN PATENT DOCUMENTS 0373927  6/1990  European Pat. Off. ............ 606/180

*Primary Examiner*—Edgar S. Burr
*Assistant Examiner*—Anthony H. Nguyen

[57] ABSTRACT

The Dottering Auger Catheter system is designed for penetration of tight stenoses or total occlusions (called blockages) as a precursor to balloon angioplasty, atherectomy, or any other vessel opening means that requires an initial passageway. Specifically, the Dottering Auger Catheter system consists of a centering catheter and a Dottering auger catheter which is a catheter that opens a passageway through an arterial blockage by passing its wedge shaped distal end through that blockage causing outward plastic deformation of the plague; i.e., angioplasty. A centering catheter that surrounds the Dottering Auger Catheter can be used to center the distal end of the auger catheter just proximal to the blockage. The purpose of the auger type of Dottering catheter is to penetrate through the blockage by means of a self-tapping screw at the catheter's distal end. Once the first thread of the screw is pushed into the blockage, rotation of the catheter resulting from turning a handle at the catheter's proximal end will cause the screw to pull itself through the blockage while a push force on the handle is also applied. Once the auger has Dottered a passageway through the blockage, the auger catheter is removed and replaced with a guide wire. Once the guide wire is in place through the newly opened passageway, the centering catheter is removed and conventional balloon angioplasty or atherectomy can be performed to further enlarge the hole through the blockage thus restoring adequate blood flow.

9 Claims, 2 Drawing Sheets

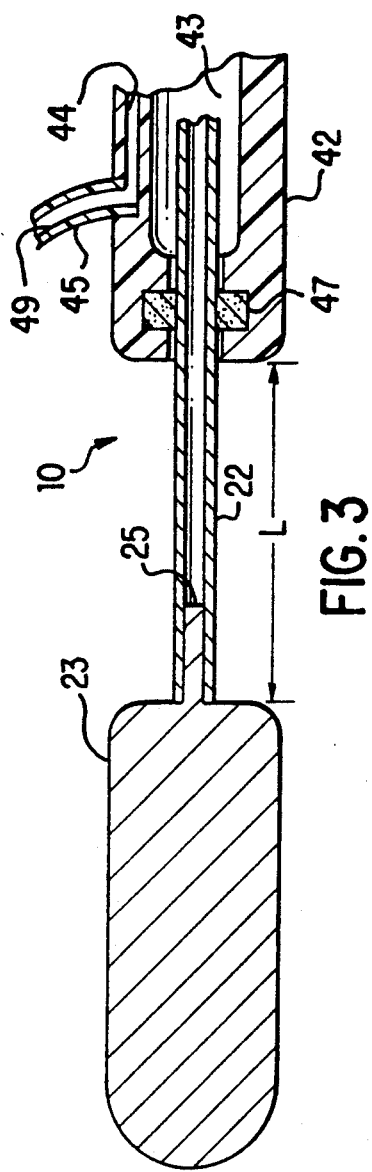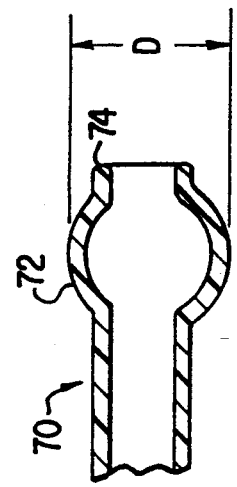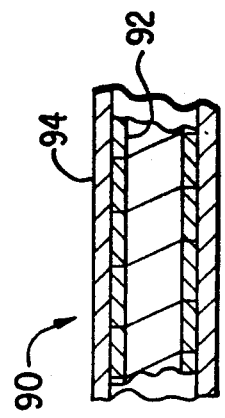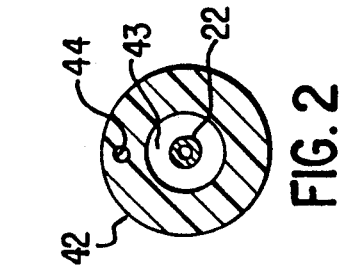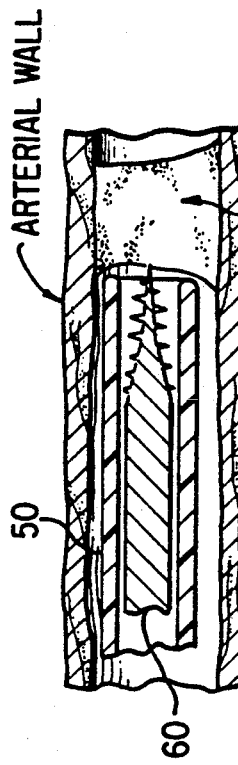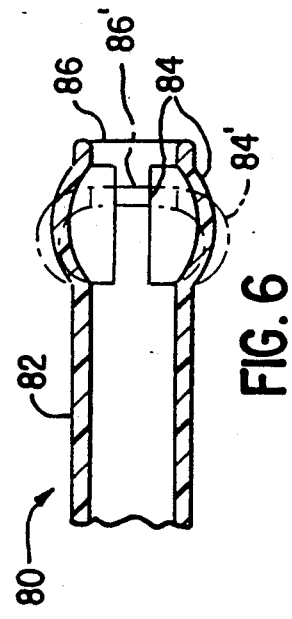

DOTTERING AUGER CATHETER SYSTEM AND METHOD

FIELD OF USE

The Dottering Auger Catheter (DAC) system described herein is intended to be used for penetration through a vessel blockage within a living body so as to make a first passageway prior to balloon angioplasty or atherectomy.

BACKGROUND

Balloon angioplasty and atherectomy are well known modalities for opening vessels of a human body particularly arteries. However, if there is an arterial blockage which cannot be penetrated by a guide wire and/or a balloon angioplasty or atherectomy catheter, surgical bypass vessel grafting is usually required to restore adequate blood flow to that blocked artery. Although lasers have been used for making a passageway, (even through a total blockage) laser equipment is expensive and laser treatment can result in removal of tissue from the arterial wall which could require surgical repair.

SUMMARY OF THE INVENTION

The present invention is a catheter system which makes possible the penetration of tight stenoses or total occlusions (called blockages) as a precursor to balloon angioplasty, atherectomy, or any other vessel opening means that requires an initial passageway. Specifically, the Dottering Auger Catheter (DAC) system consists of a centering catheter and a Dottering auger catheter. One embodiment of the centering catheter employs a distally located inflatable balloon mounted on a catheter tube to center the distal end of the auger catheter just proximal to the blockage. The purpose of the auger catheter is to penetrate through the blockage by means of a self-tapping screw at the catheter's distal end. Once the first thread of the screw is pushed into the blockage, rotation of the catheter will cause the screw to pull itself through the blockage while a push force on the catheter is also applied.

Once the auger has Dottered a passageway through the blockage, the auger catheter is removed and replaced with a guide wire. Once the guide wire is in place through the newly opened passageway, the balloon is deflated, the centering catheter is removed and conventional balloon angioplasty or atherectomy can be performed to enlarge the passageway thus restoring adequate blood flow.

An advantage of the DAC system is that, if the auger inadvertently penetrates through the arterial wall, it can be withdrawn without the removal of tissue from the vessel wall. Hence, the vessel wall would typically seal itself without the requirement of surgical repair. If a laser beam were used to open a blockage, inadvertent passage of the beam through the arterial wall would result in wall tissue removal which could require surgical repair.

Other embodiments of the DAC system described herein include various non-balloon centering catheters and a needle-tipped penetrating catheter for pushing through the blockage.

Furthermore, if a guide wire is used to try to penetrate through a blockage, it occasionally causes intimal dissection. The present invention by using a centering catheter and an auger is more likely to be able to penetrate through the blockage without causing intimal dissection.

Thus it is an object of this system to provide a Dottering Auger Catheter (DAC) system which is capable of penetrating a tight stenosis or total occlusion (blockage) in an artery so that balloon angioplasty or atherectomy can be used subsequently for further dilation of that blockage.

Another object of this invention is to provide a means for Dottering a passageway through a tight stenosis or total blockage with a device that will not damage the artery even if the arterial wall is inadvertently penetrated.

Still another object of this invention is to utilize the DAC system to make an opening through any tubular vessel in any living body.

BRIEF DESCRIPTION OF THE DRAWINGS

FIG. 2 is a transverse cross section of the DAC at position 2—2 of FIG. 1A.

FIG. 3 is a longitudinal cross section at the DAC's proximal end showing a handle for applying push and torque to the auger catheter.

FIG. 4 is a longitudinal cross section of another embodiment of the DAC system showing a centering catheter with a uniform outer diameter.

FIG. 5 is a longitudinal cross section of another centering catheter having a spherical protrusion near its distal end.

FIG. 6 is a longitudinal cross section of another centering catheter having a plurality of expandable spokes near the catheter's distal end.

FIG. 7 is a longitudinal cross section of a centering catheter having a steel flat-wire helical coil interior structure.

DETAILED DESCRIPTION OF THE DRAWINGS

Figure 1A:
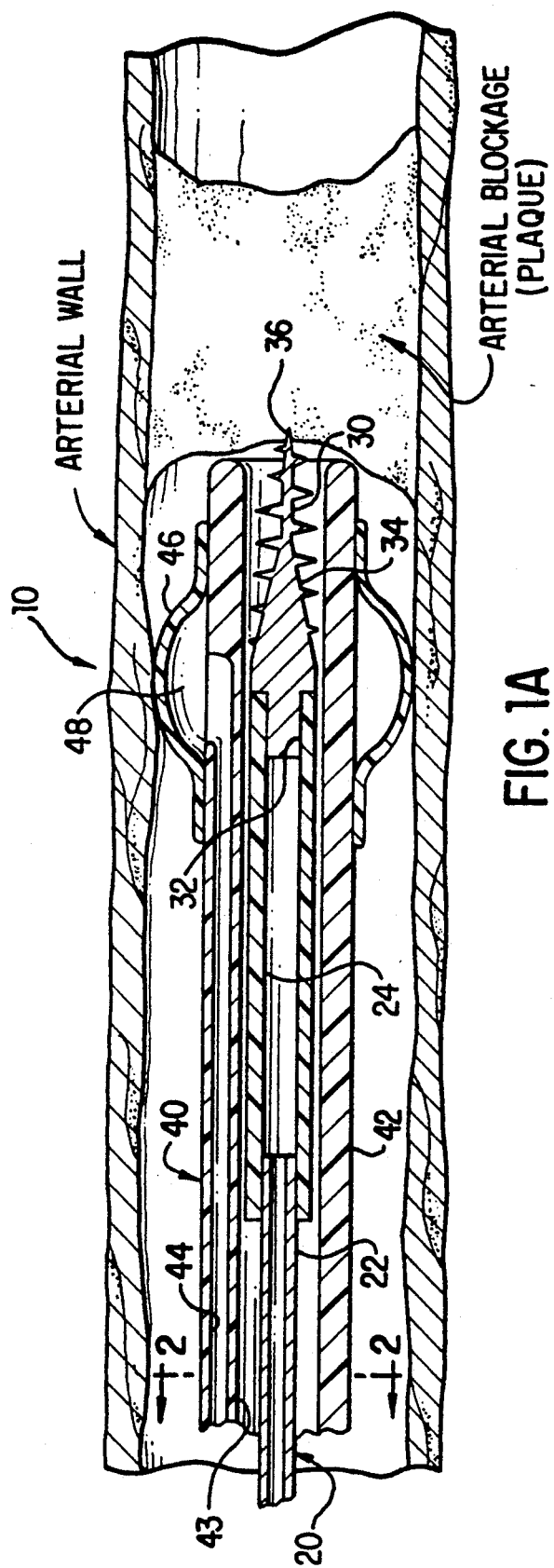
FIG. 1A is a longitudinal cross section of the distal portion of the Dottering Auger Catheter (DAC) system within an artery having a total blockage.

FIG. 1A is a longitudinal cross section showing a distal portion of the DAC system 10 within an artery which has a total occlusion (blockage). The DAC system 10 consists of the Dottering auger catheter (auger) 20 and a centering catheter 40. The auger 20 consists of a proximal steel tube 22, a flexible catheter section 24 and a distal, self-taping screw 30. The proximal end of the tube 22 extends outside of the patient's body (see FIG. 3) where a conventional handle can be mounted which facilitates the operator's ability to simultaneously apply a rotational torque (twist) and a push force to the auger 20. The tube 22 is joined at its distal end to the flexible catheter 24 which is joined at its distal end to the auger screw 30. Thus, the push and twist imparted at the proximal end of the tube 22 will be imparted to the screw 30 so that it will screw itself into the arterial blockage.

The self-tapping screw 30 consists of a shoulder 32 which is joined (typically by an adhesive or by welding) to the catheter section 24. Further the screw 30 has a conical section 34 which makes a progressively larger central opening in the plaque of the blockage as the screw 30 is advanced by rotating it and pushing it forward through the blockage. The process of enlarging a hole through a blockage by pushing forward a tapered or conically shaped nose of a catheter is called "Dottering". This Dottering process is accomplished by plastic deformation of the blockage tissue by the self-tapping screw 34 and the distal end of the flexible section 24, without any significant tissue removal. As seen in FIGS. 1A and 4, it is important to note that there is a smooth outer surface transition from the proximal end of the screw 34 onto the distal end of the flexible section 24. A smooth outer surface transition is important so that only a minimum force is required to advance the distal end of the flexible section 32 through the tissue blockage in order to accomplish Dottering of the tissue. The screw 30 also has an extremely sharp point 36 at its distal end to assist in pushing through the plaque. The screw 30 would typically be 0.5 to 2 cm. long and 0.010 to 0.060 inches in diameter.

The flexible section 24 of the auger 20 could be fabricated from a plastic such as nylon, polyethylene, polyurethane, etc. or it could be fabricated from braided metal material or made from a flat metal wire coil as is well known in the art of torque cables. The length of the flexible section 24 would typically be between 2 and 20 inches, and the outside diameter would typically be between 0.010 and 0.060 inches with a wall thickness between 0.003 and 0.020 inches.

The steel tube 22 would typically have a wall thickness between 0.002 and 0.010 inches and would be fashioned from a material such as type 304 stainless steel. The same stainless could be used for all other metal parts of the DAC system 10 such as the screw 30.

The centering catheter 40 consists of a plastic tube 42 having a central lumen (or passageway) 43 through which the auger 20 can be passed, and a second lumen 44 through which a fluid such as air or contrast medium can be passed in order to inflate the balloon 46 that is located near the distal end of the centering catheter 40. Such a fluid will fill the chamber 48 that lies internal to the balloon 46 thus centering the distal ends of the tube 42 and the central lumen 43 within the artery. Thus, the distal end of the auger 20 which lies within the lumen 43 will also tend to be centered so that the point 36 will be centered onto the proximal surface of the blockage. Thus the auger 20 can be pushed through the blockage near its center which reduces the possibility that the screw 30 will penetrate through the arterial wall. Even if it does penetrate through the arterial wall, the screw 30 could be screwed back without resulting in serious harm to the patient. This is because no piece of arterial wall would actually be removed by the screw 30 as would be the case if a laser beam or cutting blade actually removed a piece of the arterial wall. An inadvertent penetration of the arterial wall with the auger would tend to be self-sealing.

Figure 1B:
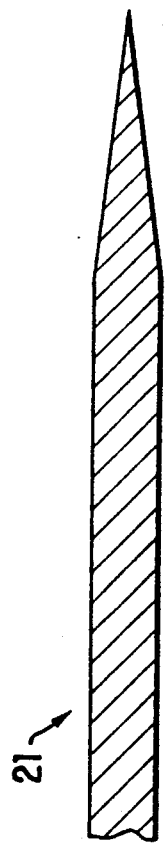
FIG. 1B is a longitudinal cross section of a penetration catheter to be used within a centering catheter.

FIG. 1B shows an alternative embodiment of the auger catheter 20 shown in FIG. 1A. Specifically, the penetration catheter 21 shown in FIG. 1B would pass through the central passageway of a centering catheter and could penetrate through a blockage by pushing or with the assistance of ultrasonic vibration applied at its distal end. Like the auger 20, the penatration catheter 21 would not remove tissue and would be centered by the centering catheter as it passes through the blockage which reduces the possibility of intimal dissection and/or arterial wall perforation.

FIG. 2 shows a cross section of the DAC system 10 at position 2—2 of FIG. 1A. At the center is the auger tube 22 which can slide within the central lumen 43 of the catheter tube 42. The lumen 44 forms a passageway for fluid to inflate or deflate the balloon 46.

FIG. 3 illustrates the proximal end of the DAC system 10 which lies outside of the patient's body. The proximal end of the tube 42 would terminate in a hemostasis valve 47 formed as a soft elastomer seal. This valve 47 seals against the outer surface of the steel tube 22. A side arm 45 near the proximal end of the tube 42 has a lumen 49 which is in fluid communication with the balloon lumen 44. Thus inflation and deflation of the balloon 46 (of FIG. 1A) can be accomplished by injecting fluid through the lumen 49 of the side port 45. The design of the valve 47 and side arm 49 would be typical of valve and side port designs used at the proximal end of the introducer sheaths which are well known in this art.

A steel handle 23 formed as shown in FIG. 3 would be joined by spot welding through the proximal end of the tube 22 onto the extension 25 of the handle 23. Other handle designs could be accomplished by plastic molding onto the proximal end of the tube 22.

The total lengths of the centering catheter 40 and the auger 20 can be predetermined so that the length "L" shown in FIG. 3 is an exactly known length when the point 36 is co-extensive with the distal end of the centering catheter 40. For example, with the geometry of the distal end of the DAC system 10 as shown in FIG. 1A, when the point 36 extends (let us say) 1.0 mm beyond the distal end of the centering catheter 40, then the dimension "L" might be 1.9 cm. Thus the most that the screw 30 could be advanced through a blockage would be 2.0 cm. Further, the outer surface of the tube 22 within the length "L" shown in FIG. 3 could have marks which indicate to the doctor how far the point 36 has advanced beyond the centering catheter's distal end.

The procedure for using the DAC system 10 based on the embodiment of FIGS. 1A, 2 and 3 would be as follows:

(1) Angiography would be used to indicate an arterial blockage.
(2) A 0.038 inch diameter guide wire would then be advanced through an introducer sheath at the patient's groin (and possibly through a guiding catheter) until the guide wire's distal end touches the proximal surface of the blockage.
(3) The centering catheter would then be advanced over the guide wire until its distal end is in contact with the blockage's proximal surface.
(4) The guide wire would then be removed and the balloon would be inflated to a moderate pressure such as 5 psi.
(5) Contrast medium would then be injected through the central lumen of the centering catheter to verify its position in the artery. The length of the blockage would be noted.
(6) An auger having a diameter of 0.038 inches would then be advanced through the centering catheter until its distal end was in contact with the blockages.
(7) Using the scale at the proximal end of the tube 22, the auger would be advanced a distance somewhat greater that the length of the blockage by turning the auger's handle in a known direction such as clockwise while pushing it forward.
(8) The auger would then be removed and contrast medium would be injected through the central lumen of the centering catheter to verify that the auger had Dottered an opening through the blockage.

(9) A guide wire for an angioplasty balloon catheter (typically 0.014 inches diameter) would then be advanced through the centering catheter and through the newly formed passageway in the blockage.

(10) The centering catheter would then be removed and a balloon angioplasty or atherectomy procedure would be performed.

FIG. 4 shows an alternative embodiment of a centering catheter 50 having a uniform outer diameter which can be used to adequately center an auger catheter 60 inside a comparatively small artery. The centering catheter 50 is considerably simpler and therefore less costly and complex in operation as compared to the balloon centering catheter 40 of FIG. 1A. If, for example, the internal diameter of the artery is 2.0 mm, then a centering catheter 50 could have an outside diameter of 1.9 mm, a wall thickness of 0.4 mm, and the auger 60 could have an outer diameter of 1.0 mm (0.039 inches) which could readily slide within that centering catheter.

FIG. 5 shows another design of a centering catheter 70 which employs a spherically shaped bulge 72 near the catheter's distal end. This catheter 70 could have the same dimensions as the catheter 50, except the outer diameter "D" of the bulge 72 would lie between 2.0 and 6.0 mm. When pushed through a guiding catheter or introducer sheath, the bulge 72 could collapse to slide within the inside cylindrical surface of that guiding catheter or sheath. Once in an artery, the bulge would expand to accurately center the distal end 74 of the centering catheter 70 in an artery just proximal to a blockage. The distal end 74 could be made radiopaque so that it could be visualized with fluoroscopy.

FIG. 6 illustrates still another embodiment of a centering catheter 80 which has a plurality of spokes 84 near its distal end which connect to a distal ring 86. In its normal position, the spokes 86 of this 4 spoke design (3 spokes are shown in this longitudinal cross section) bulge out slightly. However, when the distal ring 84 is pushed against a blockage, the spokes 86 will bulge in an outward direction as shown by the dotted lines 84 in FIG. 6, and the distal ring 86 will move in a proximal direction to a position as indicated by the dotted lines 86.

FIG. 7 shows another centering catheter 90 in which the interior structure is a helical, flat-wire steel coil 92. One purpose of the coil 92 is to prevent the auger screw threads from catching on the interior plastic surface of the centering catheter 90. Such a metal helical coil 92 would be covered on its outer surface by a plastic tube 94 so that the centering catheter would slide smoothly within an artery. Another purpose of the coil 92 is to make the distal end of the centering catheter steerable so that the distal tip of the auger could be aimed at some angle relative to the blockage to avoid penetrating the wall in a curved artery. Composite materials catheter designs of this type are described in detail in U.S. Pat. application Ser. No. 517,213 filed on May 1, 1990 by Robert E. Fischell and entitled "A Non-Buckling Thin-Walled Sheath for Percutaneous Insertion of Transluminal Catheters"; which application is included herein by reference.

Although the discussion herein was concerned with opening an arterial blockage, the technique is also applicable to stenoses through which a guide wire can be passed but which are too tight to allow the passage of a balloon angioplasty or atherectomy catheter. Furthermore, this technique could be applied to opening other blockages of vessels in living bodies such as bile ducts, fallopian tubes, urethras, etc. through which it is desired to make a passageway. Furthermore, the centering and balloon dilation functions could both be accomplished with the same balloon angioplasty catheter.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A catheter system for forming a passageway through a blockage in a human artery comprising:

a centering catheter in the form of an elongated cylinder having proximal and distal ends, the centering catheter being adapted to be percutaneously inserted into an artery and then advanced until its distal end contacts the proximal surface of an arterial blockage;

an auger catheter having proximal and distal ends having a self-tapping screw at its distal end and also having a flexible section whose distal end is joined to the screw's proximal end, the auger catheter being adapted to be advanced within the centering catheter until a sharp point at the screw's distal end contacts the proximal surface of the blockage, the outer surface of the screw having a smooth transition from the screw's proximal end onto the flexible section's distal end, the auger catheter also having a handle at its proximal end that lies outside the patient's body, the handle and screw cooperating so that when the handle is pushed forward and rotated in a particular direction, the screw will advance in a forward direction thereby forming a passageway though the blockage by plastically deforming the blockage tissue without any significant tissue removal.

2. The catheter system of claim 1 wherein the centering catheter is of a uniform outer diameter throughout its length that lies within the patient's arterial system.

3. The catheter system of claim 1 wherein the centering catheter has a bulge near its distal end to facilitate centering of the centering catheter's distal end.

4. The catheter system of claim 3 wherein the bulge collapses inward when pushed within a guiding catheter or sheath and then expands outward after the distal end of the centering catheter extends beyond the guiding catheter or sheath.

5. The catheter system of claim 1 wherein a distal portion of the centering catheter has a plurality of spokes which are flexibly attached to a distal end ring, the spokes being adapted to bulge outwardly when the centering catheter is pushed in a forward direction after the distal ring has engaged the proximal surface of the blockage.

6. The catheter system of claim 1 wherein the centering catheter has a first and central lumen which forms a passageway for the auger, and a second lumen which is fluidically isolated from the first lumen, the second lumen allowing fluid communication between the centering catheter's proximal end and an inflatable balloon located near the centering catheter's distal end, the inflatable balloon being adapted to center the centering catheter's distal end when the balloon is inflated.

7. The catheter system of claim 1 wherein the centering catheter has a flat wire helical coil on its interior.

8. The catheter system of claim 1 wherein the centering catheter has a hemostasis valve at its proximal end which makes a fluid seal against the outer cylindrical surface of the auger catheter.

9. The catheter system of claim 1 wherein the distance that the distal end of the screw extends beyond the distal end of the centering catheter is indicated by marks on the outer surface of the auger catheter's proximal end.

* * * * *